United States Patent
Yonce et al.

(10) Patent No.: US 7,697,977 B2
(45) Date of Patent: Apr. 13, 2010

(54) METHOD AND APPARATUS FOR DETERMINING RELATIVE DEPOLARIZATION AT MULTIPLE CARDIAC SENSING SITES

(75) Inventors: David J. Yonce, Fridley, MN (US); Robert S. Harguth, Ham Lake, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 1621 days.

(21) Appl. No.: 10/306,617

(22) Filed: Nov. 27, 2002

(65) Prior Publication Data

US 2004/0102812 A1    May 27, 2004

(51) Int. Cl.
*A61N 1/362* (2006.01)
(52) U.S. Cl. .................................... 600/510
(58) Field of Classification Search ............... 607/9, 607/25, 24, 27; 600/509, 510
See application file for complete search history.

(56) References Cited

U.S. PATENT DOCUMENTS

| | | | |
|---|---|---|---|
| 4,250,889 A | 2/1981 | Levin | 600/521 |
| 5,181,511 A | 1/1993 | Nickolls et al. | 128/419 PG |
| 5,243,981 A | 9/1993 | Hudrlik | 607/11 |
| 5,265,602 A | 11/1993 | Anderson et al. | 607/9 |
| 5,331,966 A | 7/1994 | Bennett et al. | 600/508 |
| 5,995,870 A | 11/1999 | Cazeau et al. | 607/9 |
| 6,076,013 A | 6/2000 | Brennan et al. | 607/2 |
| 6,152,882 A * | 11/2000 | Prutchi | 600/509 |
| 6,223,072 B1 * | 4/2001 | Mika et al. | 600/510 |
| 6,233,487 B1 * | 5/2001 | Mika et al. | 607/27 |
| 6,360,126 B1 * | 3/2002 | Mika et al. | 607/9 |
| 6,363,277 B1 | 3/2002 | Dooley et al. | 607/9 |
| 6,704,598 B2 | 3/2004 | Ding et al. | 607/9 |
| 2001/0049542 A1 | 12/2001 | Florio et al. | 607/28 |
| 2002/0082656 A1 | 6/2002 | Stahmann et al. | 607/9 |
| 2002/0193834 A1 * | 12/2002 | Levine | 607/9 |
| 2003/0009197 A1 * | 1/2003 | Helland et al. | 607/9 |
| 2004/0098056 A1 | 5/2004 | Ding et al. | 607/9 |

FOREIGN PATENT DOCUMENTS

WO    WO-99/58191    11/1999

OTHER PUBLICATIONS

Daubert, J.-C., et al., "Clinical Effects of Biventricular Pacing in Patients with Severe Heart Failure and Normal Sinus Rhythm: Results from the Multisite Stimulation in Cardiomyopathy-MUSTIC—Group I", *Circulation, Suppl. II*, 102 (18), Abstract No. 3354, (Oct. 2000), p. II-694.

Alonso, C., et al., "ECG Predictive Factors of Positive Response to Multisite Biventricular Pacing in Advanced Heart Failure", *PACE*, 22, NASPE Abstract No. 232, (Apr. 1999),p. 758.

(Continued)

*Primary Examiner*—George R Evanisko
*Assistant Examiner*—Alyssa M Alter
(74) *Attorney, Agent, or Firm*—Schwegman, Lundberg & Woessner, P.A.

(57) ABSTRACT

A cardiac rhythm management device in which the relative depolarization times at sensing/pacing electrode sites during a cardiac contraction are determined by a bipolar sensing technique. The information gained thereby can be used to select which of the available electrodes should be used for optimal resynchronization pacing.

20 Claims, 2 Drawing Sheets

OTHER PUBLICATIONS

Alonso, C., et al., "Influence of Left and Right Ventricular Pacing Sites on QRS Characteristics during Biventricular Pacing in Advanced Heart Failure", *PACE*, 22, NASPE Abstract No. 644,(Apr. 1999),p. 861.

Alonso, C., et al., "Intravascular Extraction of Leads Chronically Implanted Into the Cardiac Veins for Permanent Left Ventricular Pacing", *PACE*, 23, NASPE Abstract No. 35,(Apr. 2000),p. 561.

Alonso, C., et al., "Long-Term Performances of Transvenous Left Ventricular Leads: A 5 Years Experience", *PACE*, 23, NASPE Abstract No. 233,(Apr. 2000),p. 611.

Auricchio, A., et al., "Acute Hemodynamic Improvement by Pacing in Patients with Severe Congestive Heart Failure", *PACE*, 20, (Feb. 1997),pp. 313-324.

Auricchio, A., et al., "Clinical and Objective Improvements in Severe Congestive Heart Failure Patients Using Univentricular or Biventricular Pacing: Preliminary Results of a Randomized Prospective Study", *JACC*, Abstract No. 1015-30,(Feb. 1998),p. 31A.

Auricchio, A., et al., "Effect of Pacing Chamber and Atrioventricular Delay on Acute Systolic Function of Paced Patients With Congestive Heart Failure", *Circulation*, (1999),pp. 2993-3001.

Auricchio, A., et al., "The Pacing Therapies for Congestive Heart Failure (PATH-CHF) Study: Rationale, Design, and Endpoints of a Prospective Radomized Multicenter Study", *Am. J. Cardiol.*, 83 (5B), (Mar. 1999),pp. 130D-135D.

Blanc, J.-J., et al., "Evaluation of Different Ventricular Pacing Sites in Patients With Severe Heart Failure", *Circulation*, 96 (10), (1997),pp. 3273-3277.

Cazeau, S., et al., "4-year experience of Biventricular pacing for congestive heart failure", *PACE*, 21, NASPE Abstract No. 8,(Apr. 1998),p. 791.

Cazeau, S., et al., "Acute Electromechanical comparison of biventricular versus conventional DDD Stimulation in congestive heart failure patients", *PACE*, 21, NASPE Abstract No. 744,(Apr. 1998),p. 975.

Cazeau, S., et al., "Biventricular pacing decreases interventricular but not intraventricular asynchrony in multisite—paced patients for congestive heart failure", *PACE*, 21, NASPE Asbract No. 9,(Apr. 1998),p. 792.

Cazeau, S., et al., "Heart Failure: Acute hemodynamic improvement provided by multisite biventricular pacing", *JACC—Abstracts*, Abstract No. 930-70, (Feb. 1997),p. 111A.

Cazeau, S., et al., "Overlap between systole and diastole in congestive heart failure patients candidates for multisite biventricular pacing", *PACE*, 21, NASPE Abstract No. 743,(Apr. 1998),p. 975.

Daubert, Jean-Claude, et al., "Clinical Effects of Biventricular Pacing in Patients with Severe Heart Faliure and Chronic Atrial Fibrillation: Results from the Multisite Stimulation in Cardiomyopathy-MUSTIC Study—Group II", *Circulation* 102 (18 Supplement), Abstact No. 3349, (Oct. 2000),p. II-693.

Daubert, J.-C., et al., "Clinical Effects of Biventricular Pacing in Patients with Severe Heart Failure and Normal Sinus Rhythm; Results from the Multisite Stimulation in Cardimyopathy-MUSTIC—Group I", *Circulation*, 102 )18 Supplement), Abstract No., 3353, (Oct. 2000),p. II-694.

Daubert, C., et al., "Outcome Patients Chronically Implanted with Biventricular Pacing Systems for Endstage Congestive Heart Failure", *PACE*, 20, NASPE Abstracts, Part II, Abstract No. 215,(Apr. 1997),p. 1103.

Daubert, J. C., et al., "Permanent Biventricular Pacing by a Transvenous Approach", *JACC*, Abtract No. 1045-110, (Feb. 1997),p. 431A.

Daubert, L. C., et al., "Permanent Let Ventricular Pacing With Transvenous Leads Into the Coronary Veins"*PACE*, 21, (Jan. 1998), p. 239-245.

Daubert, C., et al., "Use of Specifcially Dsigned Coronary Sinus Leads for Permanent Left Ventricular Pacing: Preliminary Experience", *PACE, vol. 20, NASPE Abstracts , Part II*, Abstract No. 17, (Apr. 1997), p. 1054.

Ding, J., et al., "Can Intraventricular Electromechanical Synchrony Account for the Increase in LV +dp/dt When Pacing Heart Failure Patients at Left Ventricular Lateral Wall?", *Abstracts From the 71st Scientific Sessions*, Abstract No. 1582, (1998), p. I-303.

Gras, D., et al., "First experience with coronary sinus leads used for permanent Left Ventricular pacing", *PACE*, 21, NASPE Abstract No. 141, (Apr. 1998) , p. 825.

Gras, D., et al., "Long Term Results of Cardiac Resynchronization for Heart Failure Patients: The InSync Clinical Trial", *Abstracts for the 72nd Scientific Sessions*, Abstract No. 2714, (2000) ,p. I-515.

Gras, D., et al., "Multisite Pacing as a Supplemental Treatment of Congestive Heart Failure: Preliminary Results of the Medtronic Inc. InSync Study", *PACE*, 21, (Nov. 1998) , pp. 2249-2255.

Gras, D., et al., "Permanent Cardiac Resynchronization after Sustained Clinical Improvement in Heart Failure Patients: The InSync Trial", *PACE*, 22, NASPE Abstract No. 803, (Apr. 1999) , p. 901.

Kass, D. A., et al., "Improved Left Ventricular Mechanics From Acute VDD Pacing in Patients With Dilated Cardiomyopathy and Ventricular Conduction Delay", *Circulation*, 99, (1999) ,pp.1567-1573.

Leclercq, C., et al., "Comparative Effects of Permanent Biventricular Pacing in Class III and Class IV Patients", *PACE*, 21, NASPE Abstract No., 488, (Apr. 1998) ,p. 911.

Leclercq, C., et al., "Does the Etiology of Chronic Left Ventricular Dysfunction Influence the Long Term Effects of Biventricular Pacing in Patients with Severe Heart Failure?", *PACE*, 21, NASPE Abstract No. 569,(Apr. 1998),p. 932.

Leclercq, C., et al., "Long Term Results of Permanent Biventricular Pacing in patients with Advanced Heart Failure: Comparison of Patient with Stable Sinus Rhythm and Chronic Atrial Fibrillation", *PACE*, 23 NASPE Abstract No. 329,(Apr. 2000),p. 635.

Leclercq, C., et al., "Multisite Biventricular Pacing in Advanced Heart Failure, Current Status of the French Pilot Study", *PACE*, 22, NASPE Abstract No. 134,(Apr. 1999), p. 733.

Yu, Y., et al., "Experimental Validation of Pulse Contour Methods for Estimating Stroke Volume at Pacing Onset", *Proceedings of the 20th Annual International Conference of the IEEE Engineering in Medicine and Biology Society*, 20 (1), (1998),pp. 401-404.

\* cited by examiner

METHOD AND APPARATUS FOR DETERMINING RELATIVE DEPOLARIZATION AT MULTIPLE CARDIAC SENSING SITES

FIELD OF THE INVENTION

This invention pertains to cardiac rhythm management devices such as pacemakers and implantable monitoring devices.

BACKGROUND

Cardiac rhythm management devices are implantable devices that provide electrical stimulation to selected chambers of the heart in order to treat disorders of cardiac rhythm. A pacemaker, for example, is a cardiac rhythm management device that paces the heart with timed pacing pulses. The most common condition for which pacemakers are used is in the treatment of bradycardia, where the ventricular rate is too slow. Atrio-ventricular conduction defects (i.e., AV block) that are permanent or intermittent and sick sinus syndrome represent the most common causes of bradycardia for which permanent pacing may be indicated. If functioning properly, the pacemaker makes up for the heart's inability to pace itself at an appropriate rhythm in order to meet metabolic demand by enforcing a minimum heart rate.

Pacing therapy can also be used in the treatment of heart failure, which refers to a clinical syndrome in which an abnormality of cardiac function causes a below normal cardiac output that can fall below a level adequate to meet the metabolic demand of peripheral tissues. When uncompensated, it usually presents as congestive heart failure due to the accompanying venous and pulmonary congestion. Heart failure can be due to a variety of etiologies with ischemic heart disease being the most common. It has been shown that some heart failure patients suffer from intraventricular and/or interventricular conduction defects (e.g., bundle branch blocks) such that their cardiac outputs can be increased by improving the synchronization of ventricular contractions with electrical stimulation. Other conduction defects can occur in the atria. Cardiac rhythm management devices have therefore been developed which provide electrical stimulation to the atria and/or ventricles in an attempt to improve the coordination of cardiac contractions, termed cardiac resynchronization therapy.

SUMMARY

The present invention relates to a method and apparatus for determining the relative depolarization times of myocardial sites sensed by different pacing electrodes. That information may then be used for pacing electrode selection in order to optimally deliver pacing therapy. In accordance with the invention, a cardiac rhythm management device is programmed to determine relative depolarization times during a cardiac contraction at two selected myocardial sites by connecting the sensing/pacing electrodes that sense each selected myocardial site to a differential input of a sensing amplifier and then determining the relative depolarization times from the order of the positive and negative peaks in a resulting biphasic electrogram signal

DETAILED DESCRIPTION

Applying cardiac resynchronization therapy in the most efficacious manner requires optimal selection of one or more pacing sites for the placement of pacing electrodes and, in the case of multi-site resynchronization pacing, the sequence in which pacing pulses should be output to the multiple pacing sites. One way of selecting a pacing site for resynchronization therapy is to measure the conduction delays of potential pacing sites during an intrinsic systolic contraction. One or more myocardial sites that are demonstrated to be excited later during an intrinsic contraction can then be selected as pacing sites. Pacing the late activated site, or pacing multiple sites in a sequence corresponding to their respective conduction delays, may then provide the desired resynchronization and a more coordinated contraction. As explained below, the present invention presents a technique for determining the relative depolarization times of myocardial sites sensed by two different available pacing electrodes that requires the use of only one sensing channel.

1. Exemplary Device Description

Conventional cardiac pacing with implanted pacemakers involves excitatory electrical stimulation of the heart by the delivery of pacing pulses to an electrode in electrical contact with the myocardium. The pacemaker is usually implanted subcutaneously on the patient's chest, and is connected to electrodes by leads threaded through the vessels of the upper venous system into the heart. An electrode can be incorporated into a sensing channel that generates an electrogram signal representing cardiac electrical activity at the electrode site and/or incorporated into a pacing channel for delivering pacing pulses to the site.

Figure 1:
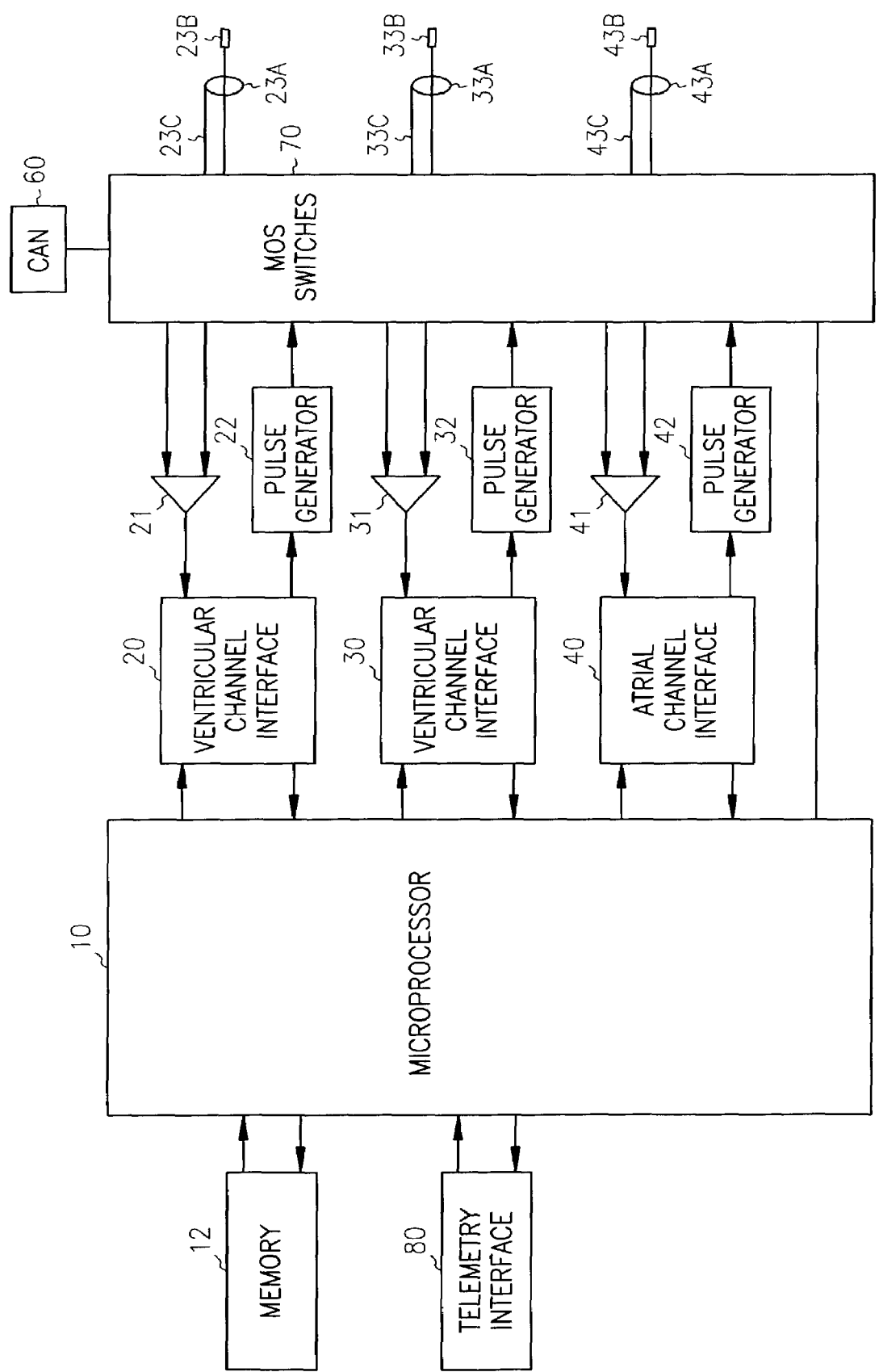
FIG. 1 is a block diagram of an exemplary cardiac rhythm management device for practicing the present invention.

A block diagram of a multi-site pacemaker having multiple sensing and pacing channels is shown in FIG. 1. (As the term is used herein, a "pacemaker" should be taken to mean any cardiac rhythm management device, such as an implantable cardioverter/defibrillator, with a pacing functionality.) The controller of the pacemaker is made up of a microprocessor 10 communicating with a memory 12 via a bidirectional data bus, where the memory 12 typically comprises a ROM (read-only memory) for program storage and a RAM (random-access memory) for data storage. The controller could be implemented by other types of logic circuitry (e.g., discrete components or programmable logic arrays) using a state machine type of design, but a microprocessor-based system is preferable. As used herein, the programming of a controller should be taken to refer to either discrete logic circuitry configured to perform particular functions or to executable code stored in memory or other storage medium. The controller is capable of operating the pacemaker in a number of programmed modes where a programmed mode defines how pacing pulses are output in response to sensed events and expiration of time intervals. A telemetry interface 80 is also provided for enabling the controller to communicate with an external programmer.

The embodiment shown in FIG. 1 has three sensing/pacing channels, where a pacing channel is made up of a pulse generator connected to an electrode while a sensing channel is made up of the sense amplifier connected to an electrode. A MOS switching network 70 controlled by the microprocessor is used to switch the electrodes from the input of a sense amplifier to the output of a pulse generator. The switching network 70 also allows the sensing and pacing channels to be configured by the controller with different combinations of the available electrodes. The channels may be configured as either atrial or ventricular channels allowing the device to deliver conventional ventricular single-site pacing with or without atrial tracking, biventricular pacing, or multi-site pacing of a single chamber. In an example configuration, a right atrial sensing/pacing channel includes ring electrode 43a and tip electrode 43b of bipolar lead 43c, sense amplifier 41, pulse generator 42, and a channel interface 40. A right ventricular sensing/pacing channel includes ring electrode 23a and tip electrode 23b of bipolar lead 23c, sense amplifier 21, pulse generator 22, and a channel interface 20, and a left ventricular sensing/pacing channel includes ring electrode 33a and tip electrode 33b of bipolar lead 33c, sense amplifier 31, pulse generator 32, and a channel interface 30. The channel interfaces communicate bi-directionally with a port of microprocessor 10 and include analog-to-digital converters for digitizing sensing signal inputs from the sensing amplifiers, registers that can be written to for adjusting the gain and threshold values of the sensing amplifiers, and registers for controlling the output of pacing pulses and/or changing the pacing pulse amplitude. In this embodiment, the device is equipped with bipolar leads that include two electrodes which are used for outputting a pacing pulse and/or sensing intrinsic activity. Other embodiments may employ unipolar leads with single electrodes for sensing and pacing. The switching network 70 may configure a channel for unipolar sensing or pacing by referencing an electrode of a unipolar or bipolar lead with the device housing or can 60.

The controller 10 controls the overall operation of the device in accordance with programmed instructions stored in memory. The controller 10 interprets electrogram signals from the sensing channels and controls the delivery of paces in accordance with a pacing mode. The sensing circuitry of the pacemaker generates atrial and ventricular electrogram signals from the voltages sensed by the electrodes of a particular channel. When an electrogram signal in an atrial or sensing channel exceeds a specified threshold, the controller detects an atrial or ventricular sense, respectively, which pacing algorithms may employ to trigger or inhibit pacing. An electrogram is analogous to a surface ECG and indicates the time course and amplitude of cardiac depolarization that occurs during either an intrinsic or paced beat.

2. Pacing Therapy

Bradycardia pacing modes refer to pacing algorithms used to pace the atria and/or ventricles in a manner that enforces a certain minimum heart rate. Because of the risk of inducing an arrhythmia with asynchronous pacing, most pacemakers for treating bradycardia are programmed to operate synchronously in a so-called demand mode where sensed cardiac events occurring within a defined interval either trigger or inhibit a pacing pulse. Inhibited demand pacing modes utilize escape intervals to control pacing in accordance with sensed intrinsic activity. In an inhibited demand mode, a pacing pulse is delivered to a heart chamber during a cardiac cycle only after expiration of a defined escape interval during which no intrinsic beat by the chamber is detected. For example, a ventricular escape interval for pacing the ventricles can be defined between ventricular events so as to be restarted with each ventricular sense or pace. An atrial escape interval can also be defined for pacing the atria either alone or in addition to pacing the ventricles. The ventricles can also be paced in an atrial tracking mode where an atrio-ventricular escape interval, triggered by an atrial sense or pace and stopped by a ventricular sense or pace, is used to pace the ventricles in synchronization with the atria.

Cardiac resynchronization therapy is pacing stimulation applied to one or more heart chambers in a manner that restores or maintains synchronized contractions of the atria and/or ventricles and thereby improves pumping efficiency. Ventricular resynchronization pacing is useful in treating heart failure in patients with interventricular or intraventricular conduction defects because, although not directly ionotropic, resynchronization results in a more coordinated contraction of the ventricles with improved pumping efficiency and increased cardiac output. Resynchronization pacing of the atria may also be beneficial in certain patients, particularly for preventing the onset of atrial arrhythmias. Resynchronization pacing usually involves delivering paces to multiple sites of either the atria or the ventricles during a cardiac cycle. The multiple pacing sites may be located in a single heart chamber, in both ventricles, or in both atria. In multi-site pacing, the atria or ventricles are paced at more than one site in order to effect a spread of excitation that results in a more coordinated contraction. Biventricular resynchronization pacing is one example of multi-site pacing in which both ventricles are paced in order to synchronize their respective contractions. Multi-site pacing may also be applied to only one chamber in order to produce a more coordinated contraction of that chamber. One way to deliver multi-site resynchronization therapy is to pace a site with a synchronous bradycardia pacing mode and then deliver one or more resynchronization paces to one or more additional pacing sites in a defined time relation to one or more selected sensing and pacing events that either reset escape intervals or trigger paces in the bradycardia pacing mode.

3. Pacing Site Selection

In a normal heartbeat, the specialized His-Purkinje conduction network of the heart rapidly conducts excitatory impulses from the sino-atrial node to the atrio-ventricular node, and thence to the ventricular myocardium to result in a coordinated contraction of both ventricles. Artificial pacing with an electrode fixed into an area of the myocardium does not take advantage of the heart's normal specialized conduction system for conducting excitation throughout the ventricles because the specialized conduction system can only be entered by impulses emanating from the atrio-ventricular node. Thus the spread of excitation from a ventricular pacing site must proceed only via the much slower conducting ventricular muscle fibers, resulting in the part of the ventricular myocardium stimulated by the pacing electrode contracting well before parts of the ventricle located more distally to the electrode.

Pacing site selection is critical for optimal application of resynchronization therapy since it is the spread of excitation after each pacing pulse that determines the manner in which the paced heart chamber contracts. Certain patients with conduction abnormalities may experience improved cardiac synchronization with conventional bradycardia pacing at a single ventricular and/or atrial site as described above because of the way in which depolarization is spread as a result of a pace as opposed to an intrinsic contraction. Thus, if a pacemaker is configured with a plurality of available pacing electrodes disposed at different pacing sites, either conventional bradycardia or resynchronization pacing can be optimized by judicious selection of which pacing electrodes are to be used. In the case of single-site bradycardia pacing, for example, it may be desirable for the paced contraction to more or less mimic an intrinsic contraction by using a pacing site that becomes depolarized before another available pacing site during an intrinsic contraction. In the case of resynchronization therapy, whether delivered as single-site or multi-site pacing, the object of the therapy is to produce a more coordinated contraction than naturally occurs. This may entail utilizing a singly paced or initially paced site that become depolarized later than other available pacing sites during an intrinsic contraction. Pacing therapy delivered in this manner thus produces a more coordinated contraction and, by reversing the spatial pattern of mechanical stresses experienced by the myocardium during an intrinsic systole, may even prevent or reverse undesirable cardiac remodeling.

4. Measurement of Depolarization Times

As explained above, pacing therapy can be more optimally delivered by a pacemaker if the pacing sites are selected among the available pacing sites in accordance with the relative depolarization times at those sites during an intrinsic contraction. Also, in the case of multi-site pacing, it may be desirable to produce a certain depolarization pattern with pacing sites selected according to relative depolarization times during a contraction resulting from a pace to the site selected for an initial pace of a multi-pace sequence. The relative depolarization times during paced or intrinsic contractions of a pacemaker's available pacing sites after implantation can be determined by configuring sensing channels with the available pacing electrodes so that a unipolar electrogram signal is generated in each channel. The time of depolarization of each available pacing site is then marked in the electrogram signal by a positive or negative peak during the contraction.

Determination of relative depolarization times by the method described above, however, involves dedicating a sensing channel to each pacing electrode whose depolarization time is to be determined for an entire paced or intrinsic cycle while the pacemaker is operating. This is problematic if the device is equipped with only one sensing channel for each heart chamber and utilizes each of the sensing channels during normal operation. In this situation, in order to determine the relative depolarization times of alternative pacing sites in one heart chamber, one heart chamber will be unsensed for an entire cardiac cycle as its sensing channel is utilized to test one of the alternative pacing electrode in another chamber. For example, in the exemplary configuration of the device in FIG. 1, the three sensing channels are normally used to sense both ventricles and the right atrium. Determining the relative depolarization times of alternative pacing sites in one of the ventricles (e.g., the sites paced by the tip electrode 23b and the ring electrode 23a) then requires the use of one sensing channel for each alternative pacing site, which means that either the other ventricle or the atria will be unsensed during the contraction in which the alternative electrodes are tested.

Figure 2A:
FIGS. 2A and 2B show examples of unipolar and bipolar electrograms.
Figure 2B:

A more economical technique for utilizing available sensing channels in order to determine the relative depolarization times of two alternative pacing sites is to determine the times from a single bipolar electrogram rather than two unipolar electrograms. The wavefront of depolarization that spreads through the myocardium during a contraction produces a potential distribution in the surrounding volume conductor that can be modeled approximately by an electrical dipole. As the depolarization wavefront approaches each of the electrodes, a positive or negative peak will be produced in the electrogram signal depending upon whether the electrode is connected to the positive or negative differential input of the sense amplifier. For example, the positive peak may represent depolarization of the electrode connected to the negative amplifier input. FIGS. 2A and 2B show examples of unipolar and bipolar left ventricular electrograms as they would be recorded from the same two left ventricular electrodes. The unipolar electrogram waveforms UWF1 and UWF2 each show a negative peak when the depolarization wavefront reaches each electrode site. The bipolar electrogram waveform BWF is biphasic with distinct positive and negative peaks PP2 and NP2, respectively, where each peak represents the depolarization of the myocardial site sensed by one of the electrodes that are connected to the differential inputs of a sense amplifier. The relative depolarization times of the two electrodes may thus be determined from the order of the positive and negative peaks in the biphasic electrogram signal. The order of the peaks can be determined by detecting each of the positive and negative peaks with analog peak detector circuitry or its digital equivalent as the electrogram signal is generated, or the electrogram signal can be digitally recorded for a period of time (e.g., 50 to 100 ms) with the peaks determined from the recording. The latter approach may be preferable in cases where the two electrodes are positioned such that the equivalent dipole of the depolarization wavefront changes its orientation as it nears the electrodes, which may cause a positively connected electrode nearest to the wavefront, for example, to generate a smaller negative peak prior to the positive peak.

Figure 3:
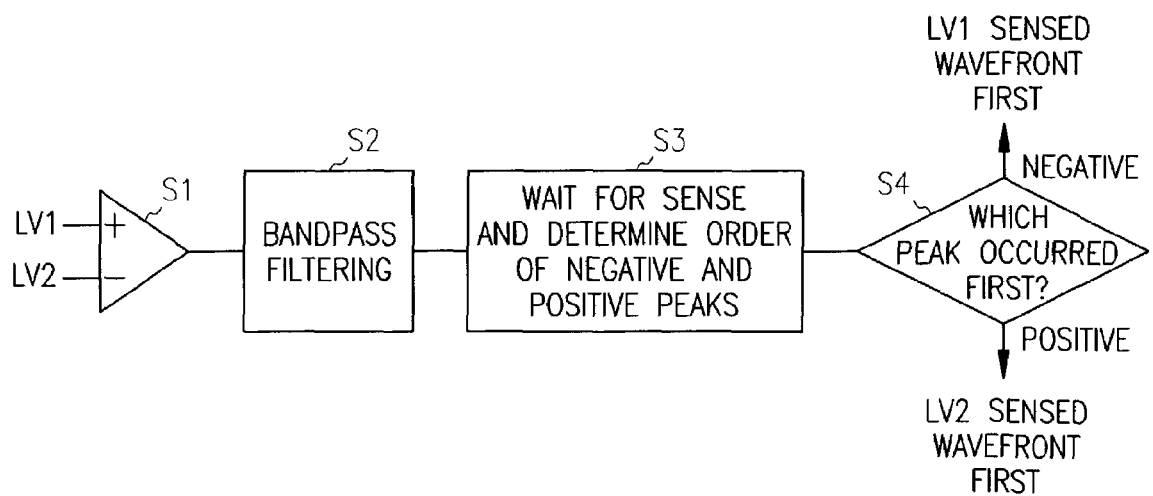
FIG. 3 shows an exemplary implementation of the technique for determining relative depolarization times of sensed sites from a bipolar electrogram.

FIG. 3 illustrates an exemplary implementation for determining the relative depolarization times of the sites sensed by two electrodes LV1 and LV2 as would be performed by an appropriately programmed device. The electrogram signals from each electrode are differentially amplified at step S1 by connecting electrodes LV1 and LV2 the positive and negative differential inputs, respectively, of a sense amplifier. For best performance, the resulting electrogram signal is then bandpass filtered at step S2 (implemented either digitally or as an analog filter). At step S3, the device waits for a sense to indicate an intrinsic contraction and then finds the location of the negative and positive peaks. (Alternatively, the device could wait for a pace output and then determine the positive and negative peaks in a bipolar evoked response electrogram.) At step S4, the device then determines that electrode LV1 sensed the wavefront first if the negative peak occurred first, or determines that electrode LV2 sensed the wavefront first if the positive peak occurred first.

The determination of depolarization times at available pacing sites by the technique described above and corresponding selection of pacing electrodes can be done by an external programmer communicating with the implanted device or automatically by the controller's programming alone. Once a pacing electrode is selected for use, the device can configure a pacing channel with the switching network that includes the selected electrode. The two electrodes whose relative depolarization times are determined may be incorporated into different leads or the same bipolar lead. In the former case, the pacing channel may be configured as a unipolar pacing channel using the selected electrode for cathodic stimulation referenced to the device housing or another spaced apart electrode. In the latter case, the pacing channel may be configured as a bipolar pacing channel with the selected electrode used as the cathode and the other electrode of the bipolar lead used as the anode.

The technique described thus allows the relative depolarization times of sites sensed by any two available sensing/pacing electrodes to be determined. A device may also be programmed to sort a group of selected myocardial sites sensed by sensing/pacing electrodes according to relative depolarization times during cardiac contractions by determining the relative depolarization times of selected pairs of the group of myocardial sites.

In one exemplary embodiment, the device controller is programmed to configure a pacing channel for bipolar pacing with first and second electrodes of a bipolar lead by selecting as a cathode whichever of the first and second electrodes senses a myocardial site last during a cardiac contraction. In another exemplary embodiment, the device controller is programmed to configure a pacing channel for bipolar pacing with first and second electrodes of a bipolar lead by selecting as a cathode whichever of the first and second electrodes senses a myocardial site first during a cardiac contraction.

Although the invention has been described in conjunction with the foregoing specific embodiments, many alternatives, variations, and modifications will be apparent to those of ordinary skill in the art. Other such alternatives, variations, and modifications are intended to fall within the scope of the following appended claims.

What is claimed is:

1. A cardiac rhythm management device, comprising:
    a plurality of electrodes for disposition near selected myocardial sites;
    a plurality of sense amplifiers for amplifying electrogram signals received from selected pairs of the plurality of electrodes;
    at least one pulse generator for outputting pacing pulses to a selected pair of the plurality of electrodes;
    a controller for controlling the output of pacing pulses and interpreting electrogram signals;
    a switching network operated by the controller for connecting a selected electrode pair to a selected sense amplifier or to a selected pulse generator;
    wherein the controller is programmed with executable instructions for performing functions which include determining relative depolarization times during a cardiac contraction at two selected myocardial sites by:
    connecting a first electrode of said plurality of electrodes disposable at a first myocardial site to one differential input of a sensing amplifier of said plurality of sense amplifiers and connecting a second electrode of said plurality of electrodes disposable at a second myocardial site to the other differential input of said sensing amplifier;
    sensing a biphasic electrogram generated by the first and second electrodes during a cardiac contraction, where the biphasic electrogram has positive and negative peaks corresponding to the cardiac contraction's depolarization at the first and second myocardial sites; and,
    determining which of the first and second myocardial sites is depolarized first during the cardiac contraction by determining that the first myocardial site is depolarized before the second myocardial site if a positive peak occurs before a negative peak in the biphasic electrogram or that the second myocardial site is depolarized before the first myocardial site if a negative peak occurs before a positive peak in the biphasic electrogram.

2. The device of claim 1 wherein the controller is programmed to determine relative depolarization times at the selected myocardial sites during an intrinsic cardiac contraction.

3. The device of claim 1 wherein the controller is programmed to determine relative depolarization times at the selected myocardial sites during a paced cardiac contraction.

4. The device of claim 1 wherein the two electrodes connected to the differential input of a sensing amplifier are incorporated into a single lead.

5. The device of claim 1 wherein the two electrodes connected to the differential input of a sensing amplifier are incorporated into different leads.

6. The device of claim 1 wherein the controller is programmed to record an electrogram signal from the two electrodes connected to the differential input of a sensing amplifier during a cardiac contraction and process the recorded electrogram signal to determine the times at which positive and negative peaks of the electrogram signal occur.

7. The device of claim 1 wherein the controller is programmed to sort a group of selected myocardial sites sensed by different electrodes according to relative depolarization times during cardiac contractions by determining the relative depolarization times of selected pairs of the group of myocardial sites.

8. The device of claim 1 wherein the controller is programmed to configure a pacing channel with an electrode selected according to the relative depolarization time of the myocardial site sensed by the electrode as compared with another myocardial site sensed by another available electrode.

9. The device of claim 1 wherein the controller is programmed to configure a pacing channel for bipolar pacing with first and second electrodes of a bipolar lead by selecting as a cathode whichever of the first and second electrodes senses a myocardial site last during a cardiac contraction.

10. The device of claim 1 wherein the controller is further programmed to configure a pacing channel for bipolar pacing with first and second electrodes of a bipolar lead by selecting as a cathode whichever of the first and second electrodes senses a myocardial site first during a cardiac contraction.

11. The device of claim 1 wherein the controller is further programmed to configure a pacing channel for unipolar pacing by selecting an electrode of a lead according to the relative depolarization time of the myocardial site sensed by the selected electrode as compared with another myocardial site sensed by another available electrode.

12. A method for operating a cardiac rhythm management device in order to determine the relative depolarization times at two selected myocardial sites, comprising:
    connecting a first electrode disposed at a first myocardial site to one differential input of a sensing amplifier and connecting a second electrode disposed at a second myocardial site to the other differential input of said sensing amplifier;
    sensing a biphasic electrogram generated from said sensing amplifiers by the first and second electrodes during a cardiac contraction, where the biphasic electrogram has positive and negative peaks corresponding to the cardiac contraction's depolarization at the first and second myocardial sites; and,
    determining which of the first and second myocardial sites is depolarized first during the cardiac contraction by determining that the first myocardial site is depolarized before the second myocardial site if a positive peak occurs before a negative peak in the biphasic electrogram or that the second myocardial site is depolarized before the first myocardial site if a negative peak occurs before a positive peak in the biphasic electrogram.

13. The method of claim 12 wherein the relative depolarization times at the selected myocardial sites are determined during an intrinsic cardiac contraction.

14. The method of claim 12 wherein the relative depolarization times at the selected myocardial sites are determined during a paced cardiac contraction.

15. The method of claim 12 wherein the two electrodes connected to the differential input of a sensing amplifier are incorporated into a single lead.

16. The method of claim 12 wherein the two electrodes connected to the differential input of a sensing amplifier are incorporated into different leads.

17. The method of claim 12 further comprising recording an electrogram signal from the two electrodes connected to the differential input of a sensing amplifier during a cardiac contraction and processing the recorded electrogram signal to determine the times at which positive and negative peaks of the electrogram signal occur.

18. The method of claim 12 further comprising sorting a group of selected myocardial sites sensed by different electrodes according to relative depolarization times during cardiac contractions by determining the relative depolarization times of selected pairs of the group of myocardial sites.

19. The method of claim 12 further comprising configuring a pacing channel with an electrode selected according to the relative depolarization time of the myocardial site sensed by the selected electrode as compared with another myocardial site sensed by another available electrode.

20. The method of claim 12 further comprising configuring a pacing channel for bipolar pacing with first and second electrodes of a bipolar lead by selecting as a cathode whichever of the first and second electrodes senses a myocardial site last during a cardiac contraction.

* * * * *